(12) United States Patent
Kawaura et al.

(10) Patent No.: US 9,955,995 B2
(45) Date of Patent: May 1, 2018

(54) PUNCTURE DEVICE AND PUNCTURE APPARATUS

(71) Applicant: TERUMO KABUSHIKI KAISHA, Shibuya-ku (JP)

(72) Inventors: Masakatsu Kawaura, Sunnyvale, CA (US); Shigeki Ariura, Ebina (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days. days.

(21) Appl. No.: 14/494,384

(22) Filed: Sep. 23, 2014

(65) Prior Publication Data

US 2015/0011820 A1 Jan. 8, 2015

Related U.S. Application Data

(63) Continuation of application No. PCT/JP2013/057061, filed on Mar. 13, 2013.

(30) Foreign Application Priority Data

Mar. 23, 2012 (JP) ................................. 2012-068399

(51) Int. Cl.
*A61B 17/34* (2006.01)
*A61B 17/04* (2006.01)
(Continued)

(52) U.S. Cl.
CPC ...... *A61B 17/3421* (2013.01); *A61B 17/0482* (2013.01); *A61B 17/06109* (2013.01);
(Continued)

(58) Field of Classification Search
CPC .... A61F 2/0004; A61F 2/0031; A61F 2/0045; A61F 2/0063; A61F 2002/0072; A61B 17/060109; A61B 2017/00805
See application file for complete search history.

(56) References Cited

U.S. PATENT DOCUMENTS 5,387,221 A * 2/1995 Bisgaard ............ A61B 17/0469
112/169
5,458,609 A 10/1995 Gordon et al.
(Continued)

FOREIGN PATENT DOCUMENTS

CN 1161640 A 10/1997
CN 1536976 A 10/2004
(Continued)

OTHER PUBLICATIONS

Supplementary Partial European Search Report dated Sep. 25, 2015, issued by the European Patent Office in corresponding European Patent Application No. EP 13 76 4048 (6 pages).
(Continued)

*Primary Examiner* — Charles A Marmor, II
*Assistant Examiner* — Carrie R Dorna
(74) *Attorney, Agent, or Firm* — Buchanan Ingersoll & Rooney PC

(57) ABSTRACT

A puncture device and method are disclosed, the puncture device includes a puncture member having a puncture needle for puncturing a biological tissue, a shaft portion, and a connection portion for connecting the puncture needle and the shaft portion to each other. The puncture needle includes a needle main body for puncturing the biological tissue, and an extension needle provided for movement relative to the needle main body along a longitudinal direction of the needle main body and configured to puncture the biological tissue. The puncture device includes, as extension means for moving the extension needle in a direction toward the distal end of the needle main body with respect to the needle main body to extend the puncture needle, and/or a pusher for pushing the extension needle to move in the direction toward the distal end of the needle main body.

20 Claims, 16 Drawing Sheets

(51) Int. Cl.
  *A61B 17/06* (2006.01)
  *A61B 17/42* (2006.01)
  *A61F 2/02* (2006.01)
  A61F 2/00 (2006.01)
  A61B 17/00 (2006.01)

(52) U.S. Cl.
  CPC .......... *A61B 17/3468* (2013.01); *A61B 17/42* (2013.01); *A61F 2/02* (2013.01); *A61B 2017/00805* (2013.01); *A61B 2017/06042* (2013.01); *A61B 2017/3443* (2013.01); *A61F 2/0045* (2013.01)

(56) References Cited

U.S. PATENT DOCUMENTS

| | | | |
|---|---|---|---|
| 6,911,003 | B2 | 6/2005 | Anderson et al. |
| 2002/0068948 | A1 | 6/2002 | Stormby |
| 2005/0277807 | A1 | 12/2005 | MacLean et al. |
| 2009/0221868 | A1* | 9/2009 | Evans .................. A61F 2/0045 600/37 |
| 2010/0274074 | A1* | 10/2010 | Khamis ............ A61B 17/00234 600/37 |

FOREIGN PATENT DOCUMENTS

| | | |
|---|---|---|
| EP | 0 582 276 A1 | 2/1994 |
| EP | 1 402 822 A2 | 3/2004 |
| JP | 06-504467 A | 5/1994 |
| JP | 10-506803 A | 7/1998 |
| JP | 2004-535835 A | 12/2004 |
| JP | 2007-260422 A | 10/2007 |
| JP | 2010-099499 A | 5/2010 |
| WO | WO 1992/012674 A1 | 8/1992 |
| WO | WO 1996/006567 A1 | 3/1996 |
| WO | WO 1998/035616 A1 | 8/1998 |
| WO | WO 2002/039890 A2 | 5/2002 |
| WO | WO 2003/075792 A1 | 9/2003 |
| WO | 2005/122909 A1 | 12/2005 |
| WO | 2008/042433 A1 | 4/2008 |

OTHER PUBLICATIONS

International Search Report (PCT/ISA/210) dated Jun. 18, 2013, by the Japanese Patent Office as the International Searching Authority for International Application No. PCT/JP2013/057061.

Office Action dated Jan. 6, 2016 by the Chinese Patent Office in corresponding Chinese Patent Application No. 201380015768(6 pages).

* cited by examiner

PUNCTURE DEVICE AND PUNCTURE APPARATUS

CROSS-REFERENCES TO RELATED APPLICATIONS

This application is a continuation of International Application No. PCT/JP2013/057061 filed on Mar. 13, 2013, and claims priority to Japanese Application No. 2012-068399 filed on Mar. 23, 2012, the entire content of both of which is incorporated herein by reference.

TECHNICAL FIELD

The present disclosure relates to a puncture device and a puncture apparatus.

BACKGROUND DISCUSSION

If a person suffers from a urinary incontinence, specifically if a person suffers from a stress urinary incontinence, then urine leakage can be caused by application of abdominal pressure during normal exercise or by laughing, coughing, sneezing and the like. The cause of this may be, for example, that the pelvic floor muscle which is a muscle for supporting the urethra is loosened by birth or the like.

For the treatment of urinary incontinence, a surgical treatment is effective, in which there is used, for example, a belt-shaped biological tissue supporting indwelling article called "sling." The sling is indwelled inside the body and the urethra is supported by the sling (for example, U.S. Pat. No. 6,911,003). In order to indwell the sling inside the body, an operator would incise the vagina with a surgical knife, dissect a region between the urethra and the vagina, and communicate the dissected region and the outside with each other through an obturator foramen using a puncture needle or the like. Then, in such a state, the sling is indwelled into the body.

However, if the vagina is incised once, a situation may occur that the sling is exposed to the inside of the vagina from a wound caused by the incision of the vagina, and complications may be caused by an infection from the wound or the like. Further, since the vagina is incised, there is such a defect that the invasion is great and the burden on the patient is heavy. Further, the urethra or the like may be damaged in the course of the procedure by the operator. In addition, the fingertip of the operator may be damaged or injured.

SUMMARY

In accordance with an exemplary embodiment, a puncture device and a puncture apparatus are disclosed, by which a biological tissue supporting indwelling article can be buried into a living body, in which the burden on the patient is relatively light, the safety of the patient is relatively high and also the safety of the operator is relatively high, and which can be compatible also with a patient whose subcutaneous tissue has a comparatively large thickness.

In accordance with an exemplary embodiment of the present disclosure, a puncture device can include a puncture needle including a needle main body for puncturing a biological tissue, and an extension needle provided for movement relative to the needle main body along a longitudinal direction of the needle main body for puncturing the biological tissue and extension means for moving the extension needle in a direction toward a distal end of the needle main body with respect to the needle main body to extend the puncture needle.

In accordance with an exemplary embodiment, the puncture device of the present disclosure is configured such that the needle main body has a hollow portion, and the extension needle is inserted in the hollow portion of the needle main body for movement along the longitudinal direction of the needle main body.

In accordance with an exemplary embodiment, the puncture device of the present disclosure is configured such that the needle main body has, at the distal end of the needle main body, an opening which communicates with the hollow portion and the extension needle has, at a distal end of the extension needle, a needle tip capable of puncturing the biological tissue, the needle tip protruding from the opening of the needle main body when the extension needle is positioned on the most proximal end side with respect to the needle main body.

In accordance with an exemplary embodiment, the puncture device of the present disclosure is configured such that the extension means has an elongated form and is inserted into the hollow portion of the needle main body to push the extension needle to move the extension needle.

In accordance with an exemplary embodiment, the puncture device of the present disclosure is configured such that the extension needle has a hollow portion, and the extension means is inserted into the hollow portion of the extension needle to push a distal end portion of the extension needle to move the extension needle.

In accordance with an exemplary embodiment, the puncture device of the present disclosure further includes an elongated biological tissue supporting indwelling article for being buried into a living body and supporting a biological tissue.

In accordance with an exemplary embodiment, the puncture device of the present disclosure is configured such that the extension means has, at a distal end portion of the extension means, an engaging portion for engaging with the biological tissue supporting indwelling article.

In accordance with an exemplary embodiment, the puncture device of the present disclosure is configured such that the extension needle is separable from the needle main body.

In accordance with an exemplary embodiment, the puncture device of the present disclosure is configured such that the needle main body and the extension needle individually have a flattened shape as viewed in a longitudinal direction of the needle main body and the extension needle.

In accordance with an exemplary embodiment, the puncture device of the present disclosure is configured such that the needle main body and the extension needle individually have a curved portion along a longitudinal direction of the needle main body and the extension needle.

In accordance with an exemplary embodiment, the puncture device of the present disclosure is configured such that the needle main body and the extension needle are individually provided for rotational movement.

In accordance with an exemplary embodiment, a puncture apparatus is disclosed, which includes a puncture device as disclosed herein, a urethral-insertion member of a longitudinal shape for being inserted into a urethra and restriction means for restricting a positional relation between the puncture needle and the urethral-insertion member such that, when the puncture needle rotationally moves and punctures the biological tissue, a needle tip of the extension needle passes a farther-position side from a center of the rotational movement of the puncture needle than the urethral-insertion member.

In accordance with an exemplary embodiment, the puncture apparatus of the present disclosure further includes a vaginal insertion member of a longitudinal shape for being inserted into a vagina, wherein the restriction means restricts the positional relation between the puncture needle and the vaginal insertion member such that, when the puncture needle rotationally moves and punctures the biological tissue, the needle tip of the extension needle does not collide with the vaginal insertion member.

In accordance with an exemplary embodiment, the puncture apparatus of the present disclosure is configured such that the puncture device has a shaft portion serving as a rotational shaft for the rotational movement, and the restriction means includes supporting members which support the shaft portion for rotational movement and respectively support the urethral-insertion member and the vaginal insertion member.

In accordance with an exemplary embodiment of the present disclosure, a biological tissue supporting indwelling article can be buried into a living body readily, and when the biological tissue supporting indwelling article is buried, the burden on the patient is relatively light and the safety of the patient is relatively high. In addition, the safety of the operator is relatively high. Further, the puncture device and the puncture apparatus can cope also with a patient who has a comparatively thick subcutaneous tissue.

For example, where the puncture apparatus includes the restriction means for restricting the positional relation between the puncture needle and the urethral-insertion member such that, when the shaft portion rotationally moves and the puncture needle punctures the biological tissue, the needle tip of the extension needle passes the farther-position side from the center of a portion, which is curved in an arc, of the extension needle, than the urethral-insertion member, for example, when the puncture apparatus is to be used for the treatment of woman's urinary incontinence, the urethral-insertion member of the puncture apparatus is inserted into a urethra, and the puncture needle is rotationally moved so that the living body is punctured by the puncture needle. Thereupon, since the needle tip of the extension needle passes the farther-position side from the center of the extension needle than the urethral-insertion member, the puncture needle can puncture the living body avoiding the urethra. Consequently, the puncture needle can be prevented from puncturing the urethra. In addition, the puncture apparatus can help prevent a fingertip of the operator from being punctured by the puncture needle.

Since the puncture needle can be extended, the puncture device and the puncture apparatus can also cope with a patient who has a comparatively thick subcutaneous tissue.

Further, when the biological tissue supporting indwelling article for the treatment of urinary incontinence is to be buried, no incision of the vaginal wall is necessary, and the biological tissue supporting indwelling article can be buried by a low invasive manual procedure. In a case in which the vagina is incised, the biological tissue supporting indwelling article can be exposed to the inside of the vagina through a wound caused by the incision, or complications such as an infection from the wound can be prevented. Therefore, the biological tissue supporting indwelling article can be buried in relatively high safety and with relative certainty.

In accordance with an exemplary embodiment, a puncture device is disclosed, comprising: a puncture needle including a needle main body for puncturing a biological tissue, and an extension needle provided for movement relative to the needle main body along a longitudinal direction of the needle main body for puncturing the biological tissue; and a pusher for moving the extension needle in a direction toward a distal end of the needle main body with respect to the needle main body to extend the puncture needle.

In accordance with an exemplary embodiment, a method is disclosed of forming a path in living body tissue comprising: placing a puncture needle of a puncture device into a portion of a living body, the puncture needle including a needle main body for puncturing a biological tissue, and an extension needle provided for movement relative to the needle main body along a longitudinal direction of the needle main body for puncturing the biological tissue; and pushing the extension needle in a direction toward a distal end of the needle main body with respect to the needle main body to extend the puncture needle into the living body.

DETAILED DESCRIPTION

Figure 1:
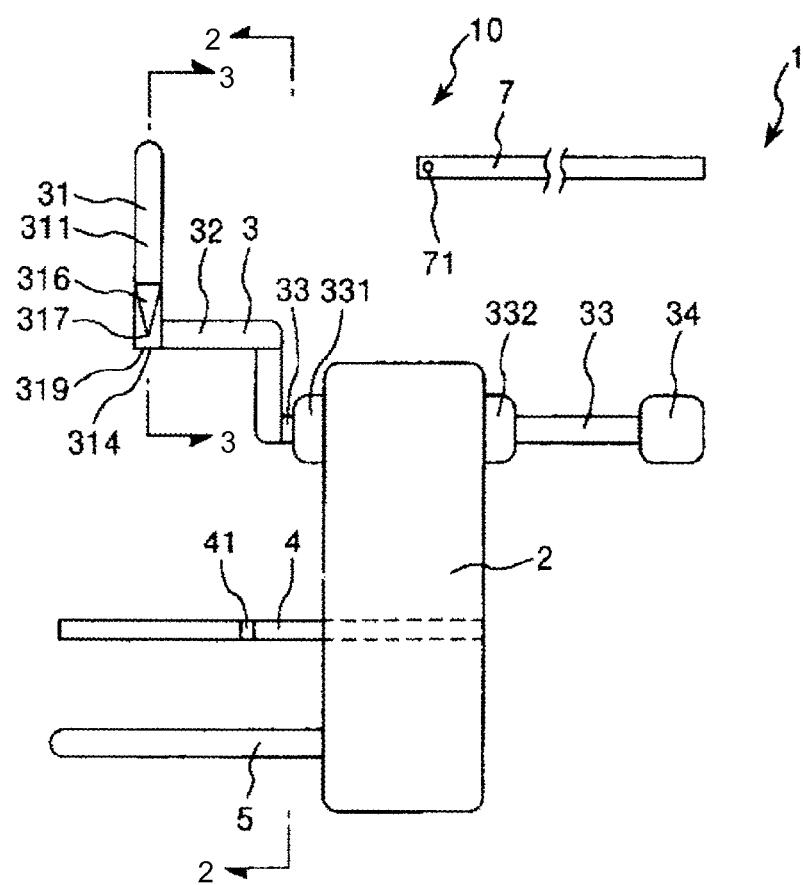
FIG. 1 is a lateral view depicting a first exemplary embodiment of a puncture apparatus of the present disclosure.

FIGS. 1-16 illustrate features and operational aspects of exemplary embodiments of the puncture apparatus as disclosed. In FIG. 5(b), FIG. 6(b), FIG. 7(b), FIG. 8(b) and FIGS. 9 to 13, slanting lines for a living body are omitted so as to be easily viewable. In FIG. 5(b), FIG. 6(b), FIG. 7(b), FIG. 8(b) and FIGS. 9 to 13, in order to facilitate understandings, a puncture member, a pusher, a biological tissue supporting indwelling article and so forth which are originally hidden by the living body and are not visible are depicted. In the description, which follows, the left side in FIG. 1, FIG. 4, FIG. 5(a), FIG. 6(a), FIG. 7(a) and FIG. 8(a) is the "distal end" and the right side is the "proximal end."

The puncture apparatus 1 shown in the drawings is an apparatus to be used for the treatment of woman's urinary incontinence, for example, to be used when a biological tissue supporting indwelling article for the treatment of urinary incontinence is buried into the inside of the living body.

The biological tissue supporting indwelling article is a buriable tool for the treatment of woman's urinary incontinence, for example, a tool to be buried into the living body for supporting the urethra (biological tissue), for example, a tool for supporting, for example, when it is intended to move the urethra to the vaginal wall side, the urethra tension-free or so as to pull the urethra in a direction in which the urethra is spaced away from the vaginal wall. For the biological tissue supporting indwelling article, for example, an elongated object having flexibility can be used.

Figure 11:
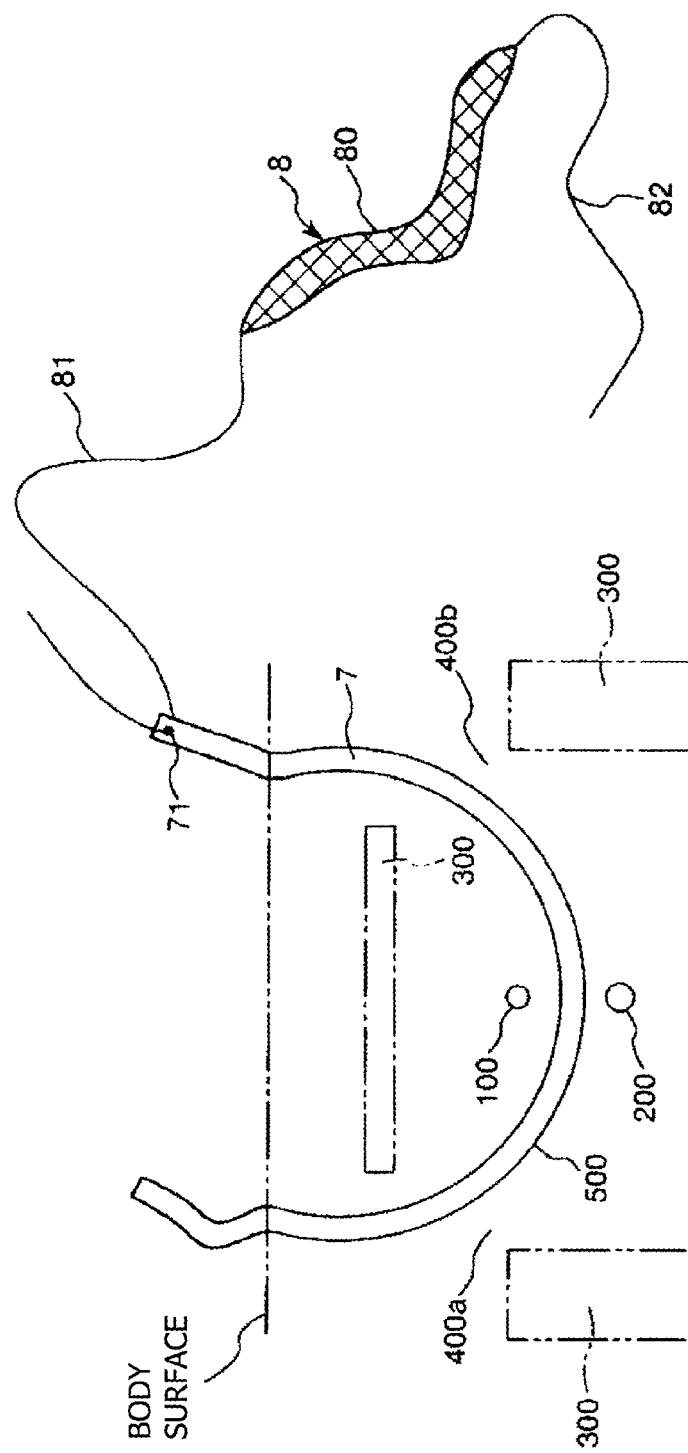
FIG. 11 is a cross sectional view illustrating an operation procedure of the puncture apparatus depicted in FIG. 1 taken along the section line 5B-5B in FIG. 5(a).

As shown in FIG. 11, in an exemplary embodiment, a biological tissue supporting indwelling article 8 can include a main body portion 80 having a belt-like shape, a string 81 fixed to one end portion of the main body portion 80, and another string 82 fixed to the other end portion of the main body portion 80. The biological tissue supporting indwelling article 8 is called a "sling." The main body portion 80 has a net-like form and can be configured, for example, as an article braided in a net-like form (lattice form) of crossing liner bodies, for example, as a braided body having a net-like form. The liner bodies may be, for example, those having a circular transverse sectional shape, those having a flattened transverse sectional shape, for example, those of a belt-like form (ribbon form), and so forth.

Further, the constituent material of the main body portion 80 of the biological tissue supporting indwelling article 8 is not limited particularly, for example, various kinds of resin materials and the like which have biocompatibility can be used.

Further, the constituent materials of the strings 81 and 82 are not limited particularly, for example, various kinds of resin materials, fibers and the like can be used.

The main body portion 80 is also not limited to that of a net-like form described hereinabove.

Figure 2:
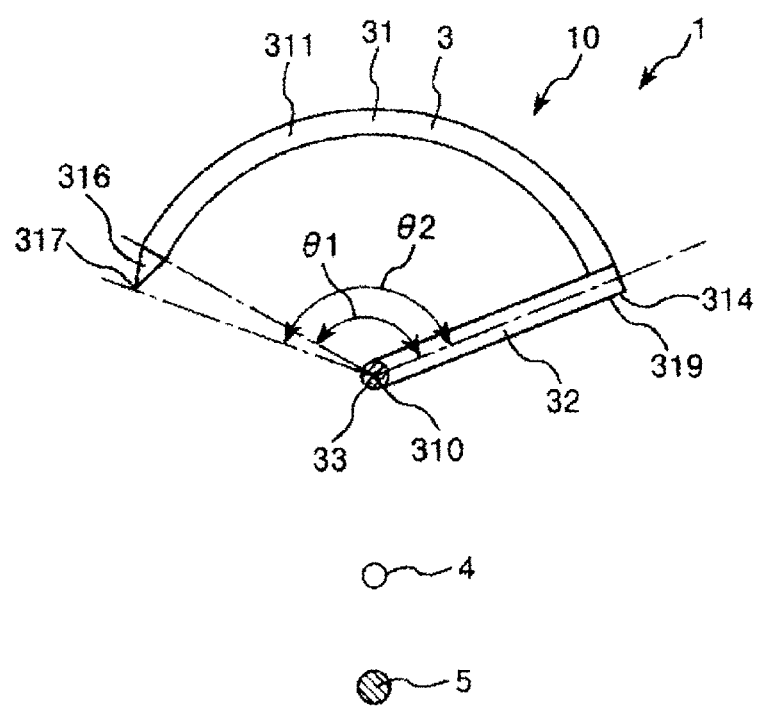
FIG. 2 is a cross sectional view taken along line 2-2 in FIG. 1.
Figure 3:
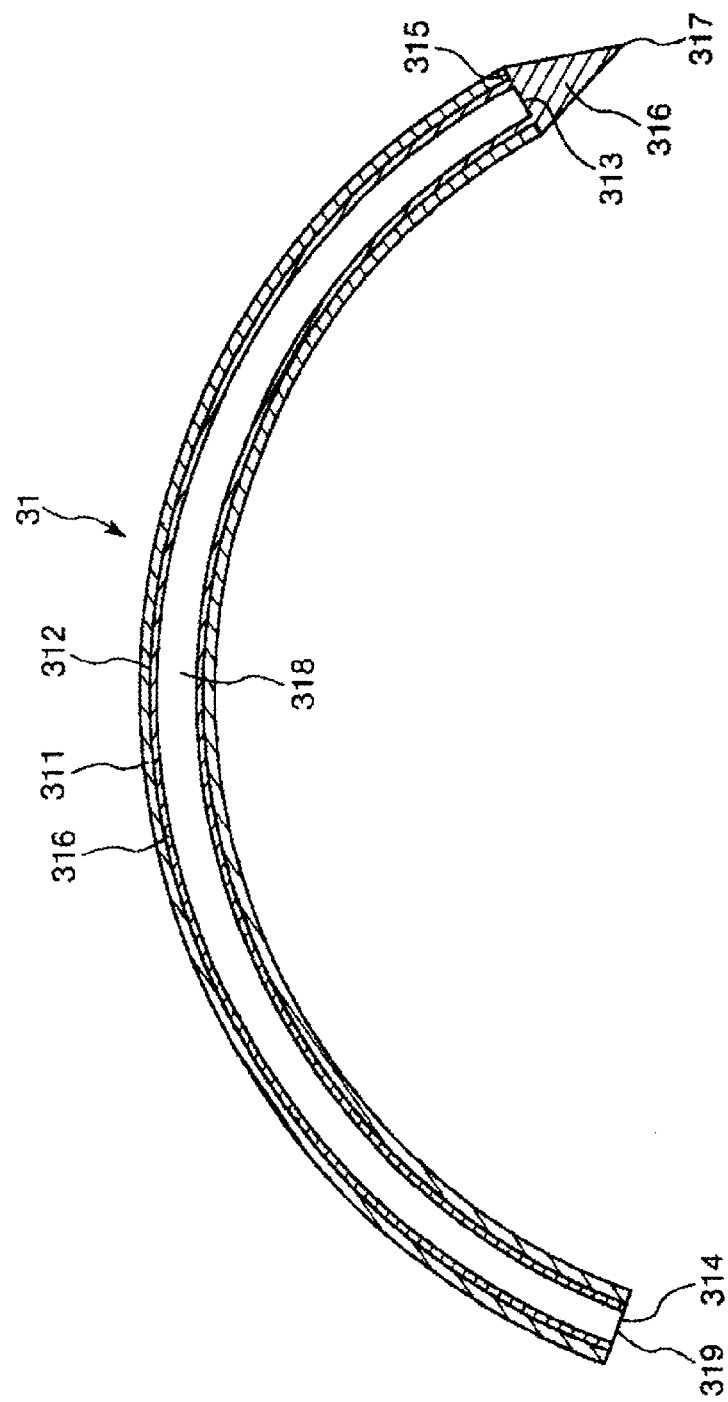
FIG. 3 is a cross sectional view taken along line 3-3 in FIG. 1 of a puncture needle of the puncture apparatus depicted in FIG. 1.

As depicted in FIGS. 1 to 3, the puncture apparatus 1 can include a puncture needle 31 for puncturing a biological tissue, a puncture member 3 including a shaft portion 33 and a connection portion 32 for connecting the puncture needle 31 and the shaft portion 33 to each other, and a punctual device 10 including the biological tissue supporting indwelling article 8. Note that the connection portion 32 connects the shaft portion 33 and a needle main body 311, to be described later, of the puncture needle 31 to each other. The puncture apparatus 1 further includes a urethral-insertion member 4 of a longitudinal shape for being inserted into a urethra, a vaginal-insertion member 5 of a longitudinal shape for being inserted into a vagina, and a supporting member (restriction means) 2 for supporting the puncture member 3, urethral-insertion member 4 and vaginal-insertion member 5.

Figure 4:
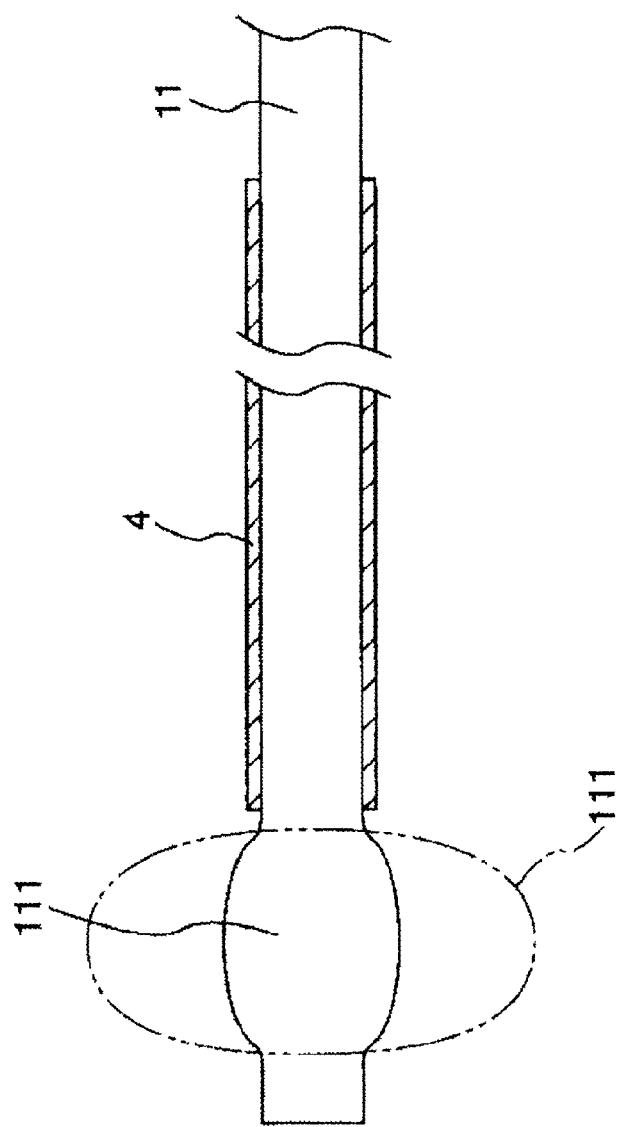
FIG. 4 is a cross sectional view illustrating a state in which a balloon catheter is inserted in a urethral-insertion member of the puncture apparatus depicted in FIG. 1.

In an exemplary embodiment, the urethral-insertion member 4 is firmly fixed to the supporting member 2. The urethral-insertion member 4 may be removably provided on the supporting member 2. The urethral-insertion member 4 has a straight tubular shape, and an opening at the proximal end of the urethral-insertion member 4, which is open at the proximal end face of the supporting member 2. Into the urethral-insertion member 4, various kinds of elongated medical tools can be inserted, such as, for example, a balloon catheter 11, which includes an expandable and contractible balloon 111 at the distal end portion of the balloon catheter 11 as depicted in FIG. 4. In FIG. 4, the balloon 111 in a contracted state is indicated by a solid line, and the balloon 111 in an expanded state is indicated by an alternate long and two-short dashes line.

The balloon 111 of the balloon catheter 11 functions as a restriction unit for restricting the position of the urethral-insertion member 4 in the axial direction (longitudinal direction) inside the urethra. More specifically, when the puncture apparatus 1 is to be used, the balloon 111 is inserted into the bladder of a patient, and the positional relation in the axial direction between the balloon catheter 11 and the urethral-insertion member 4 is fixed. Besides, the balloon 111 is caught by the bladder neck in a state in which the balloon 111 is expanded, and consequently, the position of the urethral-insertion member 4 with respect to the bladder and the urethra is fixed.

In accordance with an exemplary embodiment, a balloon expanding tool such as, for example, a syringe not depicted is connected to a port not depicted which communicates with a lumen not depicted which communicates with the balloon 111 of the balloon catheter 11. Then, operating fluid supplied from the balloon expanding tool is sent into or extracted from the inside of the balloon 111 thorough the aforementioned lumen to carry out expansion and contraction of the balloon 111. As the operating fluid for the expansion of the balloon, a liquid, such as, for example, physiological salt solution or gas can be used.

Further, the balloon catheter 11 can be used for the urination of the patient when the puncture apparatus 1 is being used.

A marker 41 can be provided at an outer circumferential portion of the urethral-insertion member 4. The marker 41 is arranged such that the marker 41 is positioned at the urethral orifice when the urethral-insertion member 4 is inserted into the urethra and the distal end portion of the urethral-insertion member 4 is positioned just in front of the bladder.

In the present exemplary embodiment, the vaginal-insertion member 5 is firmly fixed to the supporting member 2. The vaginal-insertion member 5 may otherwise be removably provided on the supporting member 2. The vaginal-insertion member 5 has a form of a straight bar. Further, the distal end portion of the vaginal-insertion member 5 can be rounded. Consequently, the vaginal-insertion member 5 can be smoothly inserted into the vagina.

Further, the vaginal-insertion member 5 is arranged in a spaced relationship by a predetermined distance from the urethral-insertion member 4 below the urethral-insertion member 4 such that the axial line of vaginal-insertion member 5 and the axial line of the urethral-insertion member 4 extend in parallel to each other.

The constituent materials of the vaginal-insertion member 5, the urethral-insertion member 4 and the supporting member 2 are not limited specifically, and for example, various kinds of resin materials can be used.

The puncture member 3 is provided for rotation at the shaft portion 33 of the puncture member 3 on the supporting member 2.

Further, the shaft portion 33 is arranged in a spaced relationship by a predetermined distance from the urethral-insertion member 4 above the urethral-insertion member 4 such that the axial line of the shaft portion 33 and the axial line of the urethral-insertion member 4 extend in parallel to each other. Further, as viewed from the axial direction of the shaft portion 33, the shaft portion 33, urethral-insertion member 4 and vaginal-insertion member 5 lie on a straight line.

The shaft portion 33 passes through the supporting member 2 in the leftward and rightward direction in FIG. 1. On the distal end and the proximal end of the shaft portion 33, a flange 331 and another flange 332 are formed, respectively, with the supporting member 2 interposed therebetween. The movement of the shaft portion 33 in the axial direction with respect to the supporting member 2 is blocked by the flanges 331 and 332.

The puncture needle 31 includes the needle main body 311 for puncturing a biological tissue, and an extension needle 316 provided for relative movement to the needle main body 311 along a longitudinal direction of the needle main body 311 to puncture a biological tissue. In accordance with an exemplary embodiment, the puncture needle 31 is extended by movement of the extension needle 316 in a direction toward the distal end of the needle main body 311 with respect to the needle main body 311. The puncture device 10 includes, as extension means for moving the extension needle 316 in the direction toward the distal end of the needle main body 311 with respect to the needle main body 311 to extend the puncture needle 31, for example, a pusher 7 for pushing the extension needle 316 in the direction toward the distal end of the needle main body 311.

The needle main body 311 has a hollow portion 312 extending from the proximal end to the distal end of needle main body 311 and has a tubular shape. In accordance with an exemplary embodiment, the needle main body 311 has an opening 313, which communicates with the hollow portion 312, at the distal end of the main body 311, and has another opening 314, which communicates with the hollow portion 312, at the proximal end of the main body 311.

The extension needle 316 is inserted in the hollow portion 312 of the needle main body 311 for movement along a longitudinal direction of the needle main body 311. Further, the extension needle 316 can be removed from the opening 313 of the needle main body 311.

Further, the extension needle 316 has a sharp needle tip 317 at the distal end of the extension needle 316, and the needle tip 317 protrudes in a direction toward the distal end from the opening 313 of the needle main body 311.

The state of the puncture needle 31 depicted in FIG. 3 is an initial state of the puncture needle 31, and when the puncture needle 31 is in the initial state, the extension needle 316 is positioned on the most proximal end side with respect to the needle main body 311. Further, in the initial state of the puncture needle 31, the needle tip 317 of the extension needle 316 protrudes in the direction toward the distal end from the opening 313 of the needle main body 311. In accordance with an exemplary embodiment, the needle tip 317 of the extension needle 316 normally protrudes in the direction toward the distal end from the opening 313 of the needle main body 311.

Further, the extension needle 316 has a hollow portion 318 extending from the proximal end to the distal end portion of the extension needle 316, and has, at the proximal end of the extension needle 316, an opening 319 which communicates with the hollow portion 318. The opening 319 configures an entrance for the pusher 7 when the pusher 7 is inserted into the hollow portion 318. It is to be noted that the distal end portion of the extension needle 316 is closed.

Further, an attachment portion 315 is formed over a circumference on an outer periphery of a distal end portion of the extension needle 316 such that the distal end of the needle main body 311 attaches to the attachment portion 315 in the initial state depicted in FIG. 3 in which the extension needle 316 is inserted in the hollow portion 312 of the needle main body 311. Consequently, when the shaft portion 33 is moved rotationally clockwise in FIG. 3 to move (rotate) the needle main body 311 clockwise in FIG. 3, the extension needle 316 moves clockwise in FIG. 3 integrally with the needle main body 311.

The pusher 7 has an elongated shape and is inserted from the opening 319 into the hollow portion 312 of the needle main body 311, for example, into the hollow portion 318 of the extension needle 316 to push a distal end portion of the extension needle 316 to move the extension needle 316 in the direction toward the distal end of the extension needle 316. The pusher 7 has a transverse sectional shape corresponding to a transverse sectional shape of the hollow portion 318 of the extension needle 316. Further, the pusher 7 has flexibility so as to be compatible with the shape of the needle main body 311 and the extension needle 316. Since the distal end portion of the extension needle 316 is closed, the distal end portion of the pusher 7 attaches to the distal end portion of the extension needle 316 and can push the distal end portion of the extension needle 316.

Further, the pusher 7 has, at a distal end portion of the pusher 7, a through-hole 71 as an engaging portion for engaging with the biological tissue supporting indwelling article 8. The through-hole 71 extends through the pusher 7 in a direction perpendicular to the longitudinal direction of the pusher 7. Into and with the through-hole 71, one of the string 81 and the string 82 of the biological tissue supporting indwelling article 8 is inserted and engaged so that the string 81 or the string 82 is held for removal (refer to FIG. 11).

The constituent material of the pusher 7 is not limited specifically, and, for example, various resin materials, various metal materials and so forth can be used.

When the puncture needle 31 is to be extended, the pusher 7 is inserted into the hollow portion 318 through the opening 319 of the extension needle 316, and the extension needle 316 is pushed by the pusher 7 to move in the direction toward the distal end. Thereupon, since the extension needle 316 is positioned on the inner circumference side of the needle main body 311, the contact area between the extension needle 316 and the biological tissue can be made comparatively small and the puncture needle 31 can be extended readily and smoothly. Further, the burden on the patient can be reduced.

Further, the puncture needle 31, for example, the needle main body 311 and the extension needle 316, can be curved in an arc centered at the shaft portion 33 along a longitudinal direction of the puncture needle 31. Further, in FIG. 1, an axial line of the puncture needle 31 and an axial line of the shaft portion 33 cross orthogonally with each other. Consequently, when the puncture member 3 moves rotationally, the needle tip 317 of the extension needle 316 moves along the arc in a plane perpendicular to the axial line of the shaft portion 33, for example, in a plane having a normal line on the axial line.

Further, in the present embodiment, the needle tip 317 of the extension needle 316 is directed toward the counterclockwise direction in FIG. 2. However, the direction of the needle tip 317 is not limited, and the needle tip 317 may be directed otherwise toward the clockwise direction in FIG. 2.

Further, in the present exemplary embodiment, the puncture needle 31 is arranged on the proximal end side in the axial direction of the urethral-insertion member 4 with respect to the distal end portion of the urethral-insertion member 4.

The puncture needle 31 may otherwise be arranged at the same position as that of the distal end portion of the urethral-insertion member 4 in the axial direction of the urethral-insertion member 4, or may be arranged at the distal end side with respect to the distal end portion of the urethral-insertion member 4.

Here, the supporting member 2 restricts the positional relation between the puncture member 3 (puncture needle 31) and the urethral-insertion member 4 such that, when the shaft portion 33, for example, the puncture member 3, moves rotationally and the puncture needle 31 punctures the biological tissue, the needle tip 317 of the extension needle 316 passes a farther-position side from the center 310 of the puncture needle 31 (extension needle 316) than the urethral-insertion member 4 or an extension line of the urethral-insertion member 4, for example, passes below the urethral-insertion member 4 or an extension line of the same. The center 310 of the puncture needle 31 is the center of the arc of the puncture needle 31. In accordance with an exemplary embodiment, the center 310 of the puncture needle 31 is the center of the rotational movement of the puncture needle 31 (puncture member 3).

Further, the supporting member 2 can restrict the positional relation between the puncture member 3 (puncture needle 31) and the vaginal-insertion member 5 such that, when the shaft portion 33, for example, the puncture member 3 moves rotationally and the puncture needle 31 punctures the biological issue, the needle tip 317 of the extension needle 316 does not collide with the vaginal-insertion member 5 and an extension line of the same.

In accordance with an exemplary embodiment, the supporting member 2 can restrict the positional relation among the puncture member 3 (puncture needle 31), urethral-insertion member 4 and vaginal-insertion member 5 such that, when the puncture member 3 moves rotationally and the puncture needle 31 punctures the biological tissue, the needle tip 317 of the extension needle 316 passes a position between the urethral-insertion member 4 or the extension line of the same and the vaginal-insertion member 5 or the extension line of the same.

Consequently, the puncture needle 31 can puncture the biological tissue avoiding the urethra and the vaginal wall, and can help prevent the puncture needle 31 from puncturing the urethra and the vaginal wall. Further, since the puncture needle 31 can be extended, it can also cope with a patient whose thickness of the subcutaneous tissue is comparatively large.

Further, since the orbit of the needle tip 317 of the extension needle 316 is predetermined, the fingertips of the operator can avoid being punctured by the puncture needle 31.

Further, the center angle $\theta 1$ of the above-described arc of the needle main body 311, the center angle $\theta 2$ of the arc of the extension needle 316 and the center angle $\theta 3$ of the arc of the puncture needle 31 in a state in which the puncture needle 31 is extended most are not limited specifically but can be set suitably in accordance with various conditions. However, the angles mentioned are set such that, when the biological tissue is punctured by the puncture needle 31, the puncture needle 31 can enter into the body of the patient from the body surface on one side, pass below the urethra and protrude to outside of the body from the body surface on the other side. Incidentally, $\theta 3$ minus $\theta 1$ equals to $\theta 2$.

In accordance with an exemplary embodiment, for example, the center angle $\theta 1$ of the arc of the needle main body 311, preferably is about 95° to 180°, and more preferably is about 120° to 150°.

Meanwhile, for example, the center angle $\theta 3$ of the arc of the puncture needle 31 in the state in which the puncture needle 31 is extended most preferably is about 190° to 270°, and more preferably is about 200° to 250°.

Consequently, when a biological tissue is punctured by the puncture needle 31, the puncture needle 31 can reliably enter into the body from the body face on one side of the patient, pass below the urethra and protrude to the outside of the body from the body surface on the other side.

Further, at the distal end portion of the shaft portion 33, a grip unit 34 is provided as an operation unit for operating the puncture member 3 rotationally. In the present exemplary embodiment, the shape of the grip unit 34 is a rectangular solid. When the puncture member 3 is to be moved rotationally, the grip unit 34 is gripped by the fingers of a hand and is moved rotationally in a predetermined direction. In accordance with an exemplary embodiment, the shape of the grip unit 34 is not to be limited to this.

Further, the connection portion 32 in the present embodiment has an L shape. A distal end portion of the connection portion 32 is fixed to a proximal end portion of the needle main body 311, and a proximal end portion of the connection portion 32 is fixed to a distal end portion of the shaft portion 33. By the connection portion 32, the puncture needle 31 and the shaft portion 33 can be spaced by a predetermined distance from each other in the axial direction of the shaft portion 33.

The connection portion 32 and the needle main body 311 may otherwise be integrated with each other, and the connection portion 32 and the shaft portion 33 may otherwise be integrated with each other. Further, the needle main body 311, connection portion 32 and shaft portion 33 may otherwise be integrated with one another.

In accordance with an exemplary embodiment, the shape of the connection portion 32 is not limited to the disclosed embodiments.

The constituent material of the puncture member 3 is not limited specifically, and such various metal materials as, for example, stainless steel, aluminum or aluminum alloy and titanium or titanium alloy can be used as the constituent material of the puncture member 3.

In accordance with an exemplary embodiment, an operation procedure of the puncture apparatus 1, for example, a procedure when the biological tissue supporting indwelling article 8 is buried into a living body, is described.

Figure 5:
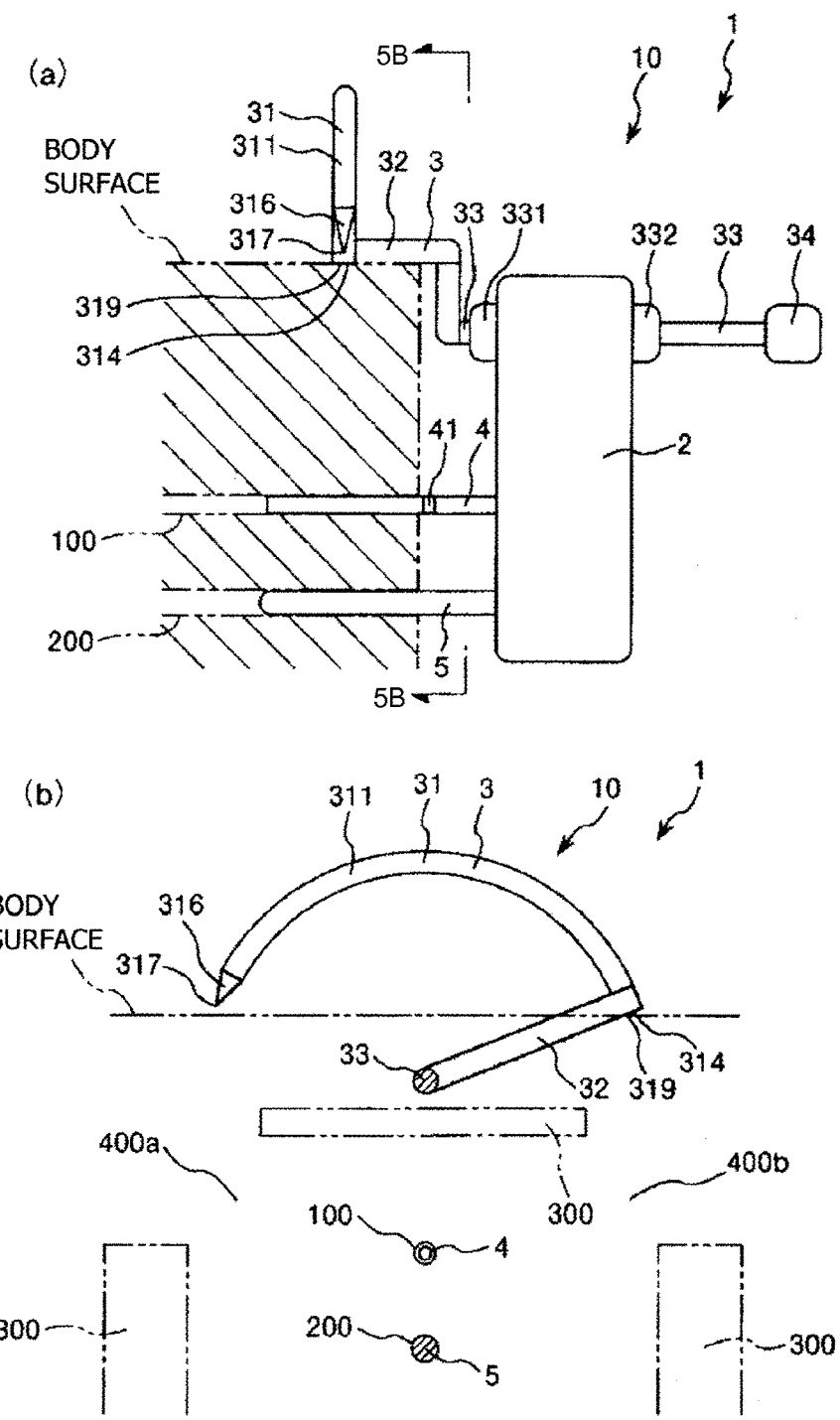
FIGS. 5(a) and 5(b) are views illustrating an operation procedure of the puncture apparatus depicted in FIG. 1 with FIG. 5(b) taken along the section line 5B-5B in FIG. 5(a).
Figure 6:
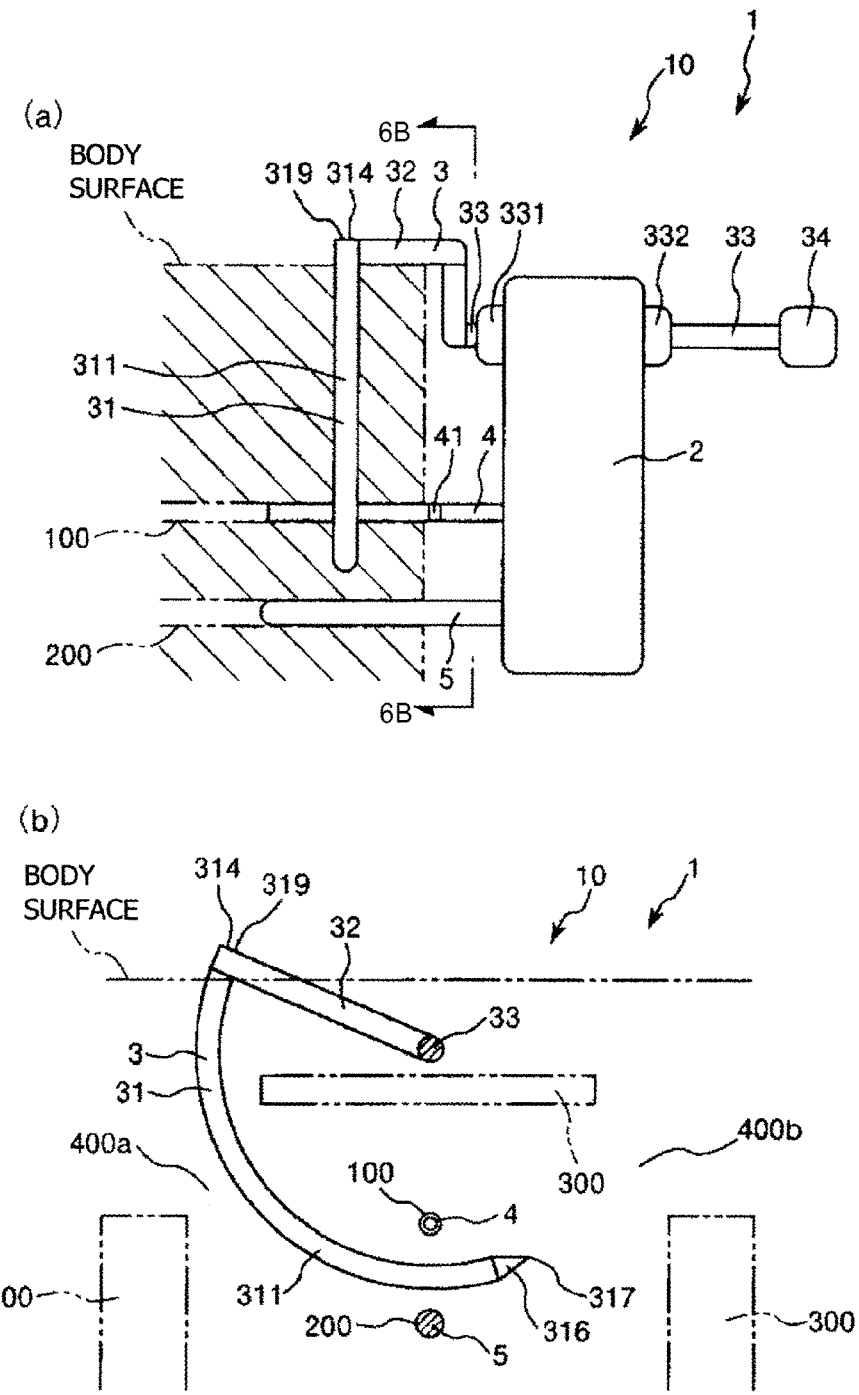
FIGS. 6(a) and 6(b) are views illustrating an operation procedure of the puncture apparatus depicted in FIG. 1 with FIG. 6(b) taken along the section line 6B-6B in FIG. 6(a).
Figure 7:
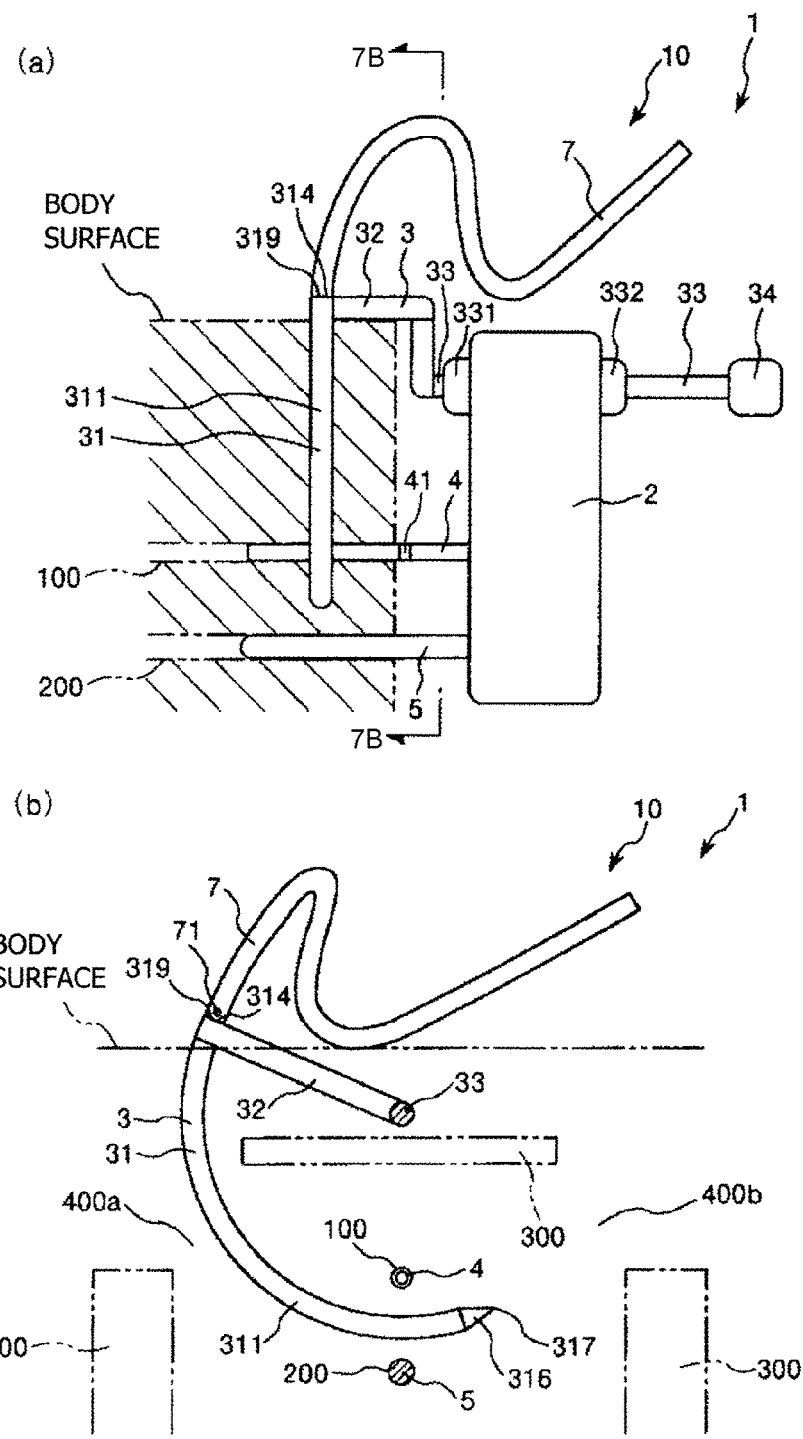
FIGS. 7(a) and 7(b) are views illustrating an operation procedure of the puncture apparatus depicted in FIG. 1 with FIG. 7(b) taken along the section line 7B-7B in FIG. 7(a).
Figure 8:
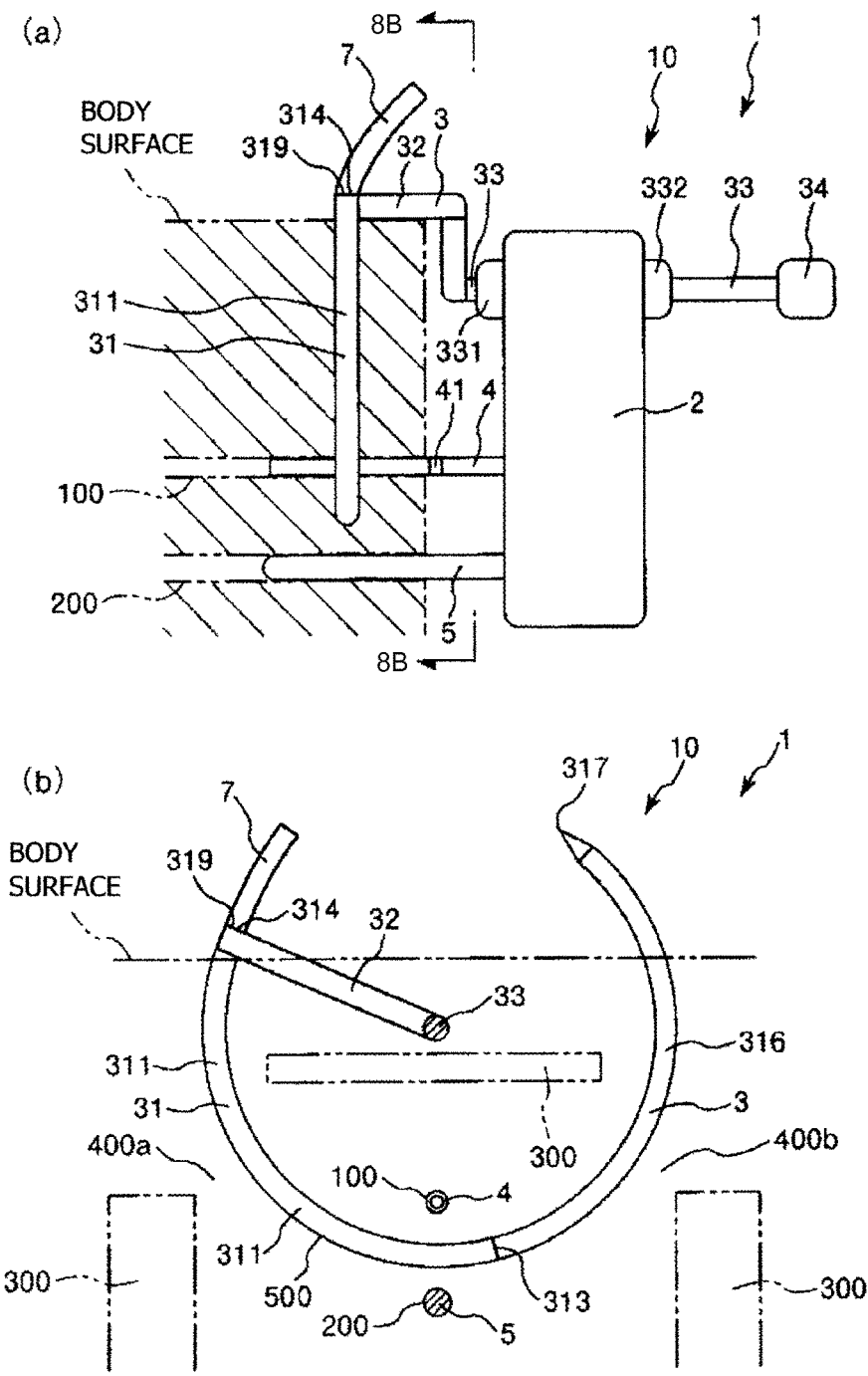
FIGS. 8(a) and 8(b) are views illustrating an operation procedure of the puncture apparatus depicted in FIG. 1 with FIG. 8(b) taken along the section line 8B-8B.

First, the puncture apparatus 1 is mounted on a patient as depicted in FIGS. 5(*a*) and 5(*b*). More specifically, the urethral-insertion member 4 of the puncture apparatus 1 is inserted into the urethra 100 of the patient and the vaginal-insertion member 5 is inserted into the vagina 200 of the patient. At the time, the insertion is carried out such that the marker 41 is positioned at the urethral orifice or on the front side of the urethral orifice. Consequently, the distal end portion of the urethral-insertion member 4 can be arranged on the front side of the bladder.

Then, the grip unit 34 is grasped as shown in FIGS. 6(a) and 6(b), and rotationally moves the puncture member 3 counterclockwise as shown in FIG. 6(b).

Consequently, the needle tip 317 of the puncture needle 31 moves counterclockwise in FIG. 6(b) along the arc of the needle tip 317; punctures the body surface at an inguinal region of the patient on the left side in FIG. 6(b) or at a region in the vicinity of the same; enters into the body; passes an obturator foramen 400a of a pelvis 300; passes below the urethra 100, for example, passes between the urethra 100 and the vagina 200; and passes an obturator foramen 400b of the pelvis 300.

Then, the pusher 7 is inserted into the hollow portion 318 through the opening 319 of the extension needle 316 as depicted in FIGS. 7(a), 7(b), 8(a), and 8(b), and the distal end portion of the extension needle 316 is pushed in a direction toward the distal end by the pusher 7 so that the extension needle 316 is moved in the direction toward the distal end.

Consequently, the needle tip 317 of the extension needle moves counterclockwise in FIG. 8(b) along the arc of the needle tip 317 and protrudes to the outside of the body from an inguinal region on the right side in FIG. 8(b) or at a region in the vicinity of the same. The distal end portion of the pusher 7 protrudes to the outside of the body from the body surface together with the extension needle 316. Consequently, in the patient, a through-hole 500 is formed which extends from the body surface at an inguinal region on the left side in FIG. 8(b) or at a region in the vicinity of the same to the body surface at an inguinal region on the right side in FIG. 6(b) or at a region in the vicinity of the same while passing through obturator foramen 400a, between the urethra 100 and the vagina 200 and through the obturator foramen 400b. The biological tissue supporting indwelling article 8 is buried in the through-hole 500.

Figure 9:
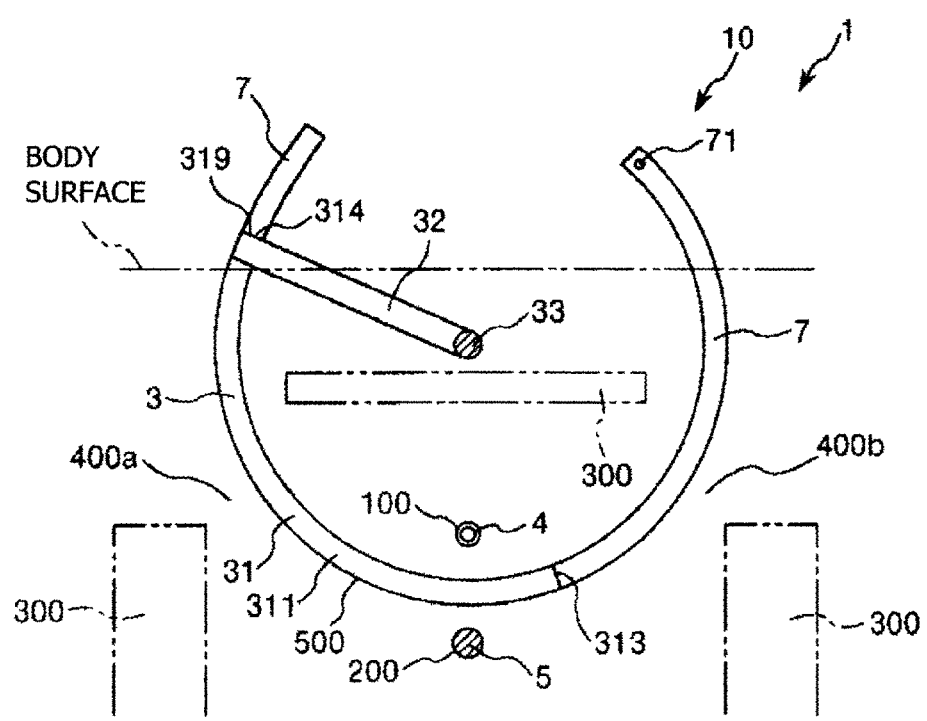
FIG. 9 is a cross sectional view illustrating an operation procedure of the puncture apparatus depicted in FIG. 1 taken along the section line 5B-5B in FIG. 5(a).

Then, the extension needle 316 is pulled in a direction toward the distal end so as to be removed from the opening 313 of the needle main body 311 as depicted in FIG. 9.

Figure 10:
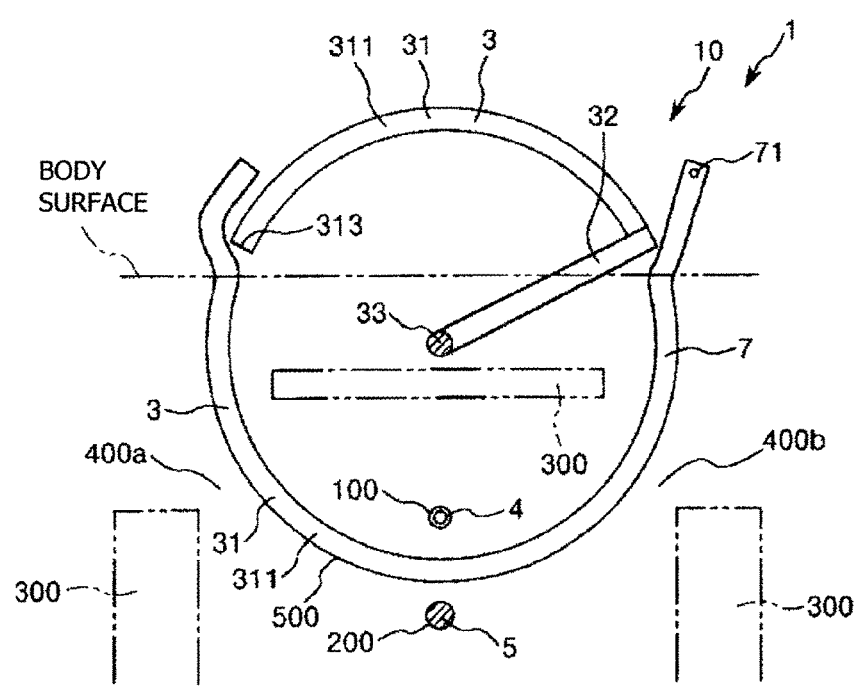
FIG. 10 is a cross sectional view illustrating an operation procedure of the puncture apparatus depicted in FIG. 1 taken along the section line 5B-5B in FIG. 5(a).

Then, as depicted in FIG. 10, the grip unit 34 is grasped and the puncture member 3 is rotated clockwise in FIG. 10.

Consequently, the distal end portion of the needle main body 311 moves along the arc of the needle body 311 clockwise in FIG. 10; passes below the urethra 100, for example, passes between the urethra 100 and the vagina 200; passes the obturator foramen 400a of the pelvis 300; and goes out to the outside of the body from the inguinal region on the left side in FIG. 10 or from the body surface in a region in the vicinity of the same. The needle main body 311 is pulled out to the outside of the body.

An end portion of one of the strings 81 and 82 of the biological tissue supporting indwelling article 8, in the configuration depicted in FIG. 11, an end portion of the string 81, is then inserted into the through-hole 71 of the pusher 7 as depicted in FIG. 11. Consequently, the end portion of the string 81 is engaged with the through-hole 71 of the pusher 7 and is held for removal by the distal end portion of the pusher 7.

The puncture apparatus 1 is then removed from the patient. In accordance with an exemplary embodiment, the urethral-insertion member 4 is pulled out from within the urethra 100 and the vaginal insertion member 5 is pulled out from within the vagina 200 of the patient.

Figure 12:
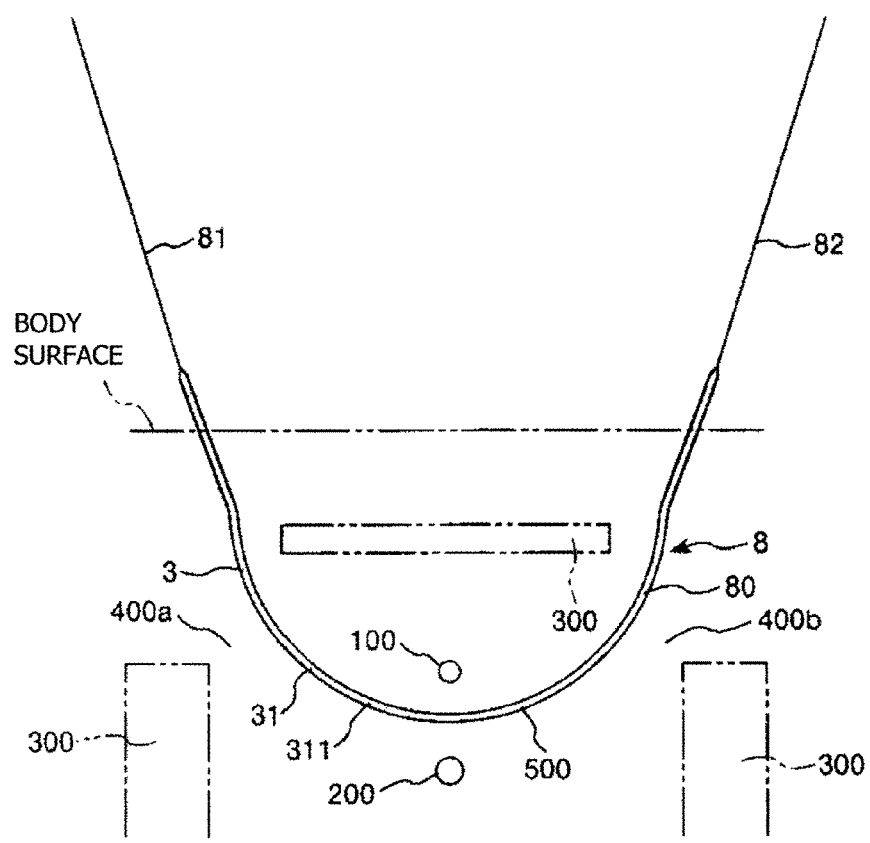
FIG. 12 is a cross sectional view illustrating an operation procedure of the puncture apparatus depicted in FIG. 1 taken along the section line 5B-5B in FIG. 5(a).

An end portion of the pusher 7 on the left side in FIG. 11 is then grasped as depicted in FIG. 12, and the pusher 7 is pulled and removed from the patient. Consequently, the end portion of the string 81 of the biological tissue supporting indwelling article 8 passes through the through-hole 500 formed in the patient and protrudes to the outside of the body from the body surface.

The string 81 is then pulled while the string 82 is pulled, and the main body portion 80 of the biological tissue supporting indwelling article 8 is inserted into the through-hole 500 formed in the patient. Then, while the end portion of the main body portion 80 on the right side in FIG. 12 is left outside the body, the end portion of the main body portion 80 on the left side in FIG. 12 is pulled out from the through-hole 500 to the outside of the body.

Figure 13:
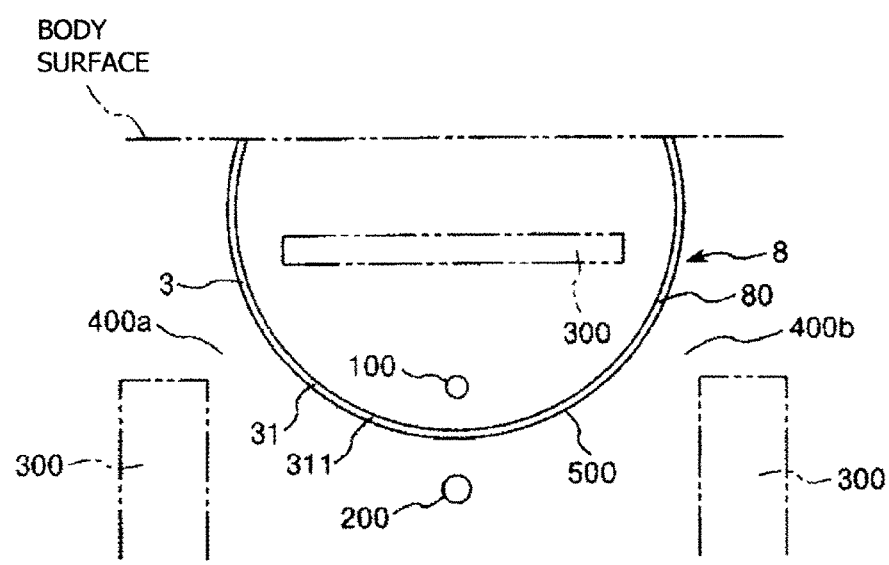
FIG. 13 is a cross sectional view illustrating an operation procedure of the puncture apparatus depicted in FIG. 1 taken along the section line 5B-5B in FIG. 5(a).

The strings 81 and 82 are then individually pulled by predetermined force as depicted in FIG. 13 to adjust the position of the main body portion 80 of the biological tissue supporting indwelling article 8 with respect to the urethra 100. Then, unnecessary portions of the biological tissue supporting indwelling article 8 are cut away and a predetermined treatment is carried out, thereby ending the manual procedure.

As described above, with the puncture apparatus 1, when the biological tissue supporting indwelling article 8 is to be indwelled, the indwelling operation can be carried out only by a low invasive manual procedure such as puncturing of the puncture needle 31. Since it is not necessary to carry out a high invasive incision or the like, the burden on the patient is relatively light and the safety of the patient is relatively high.

Further, the puncture needle 31 can puncture the living body and help avoid the urethra and the vaginal wall, and help prevent the puncture needle 31 from puncturing the urethra and the vaginal wall. Therefore, relative safety can be achieved. Further, since the puncture needle 31 extends, it can cope also with a patient who has a comparatively thick subcutaneous issue. In addition, the puncture apparatus 1 can help prevent the fingertip of the operator from being punctured by the puncture needle 31. Therefore, relative safety can be achieved.

Furthermore, the puncture needle 31 can help prevent situations such as in a conventional case in which the vagina is incised such that the biological tissue supporting indwelling article 8 is exposed to the inside of the vagina through a wound caused by the incision or complications, for example, an infection from the wound. Therefore, the biological tissue supporting indwelling article 8 can be buried in relatively high safety with relative certainty.

While, in the present exemplary embodiment, the puncture hole formed in the patient by the puncture needle 31 is a through-hole, the puncture hole is not limited to this and may not extend through the patient.

Further, the urethral-insertion member is not limited to that of a tubular shape, and may be, for example, a solid member or may be a hollow member, which is closed at one or both of the distal end portion and the proximal end portion of the hollow member.

Furthermore, at the distal end portion of the urethral-insertion member, an expandable and contractible balloon may be provided as a restriction unit for restricting the position of the urethral-insertion member in the axial direction inside the urethra.

Figure 14:
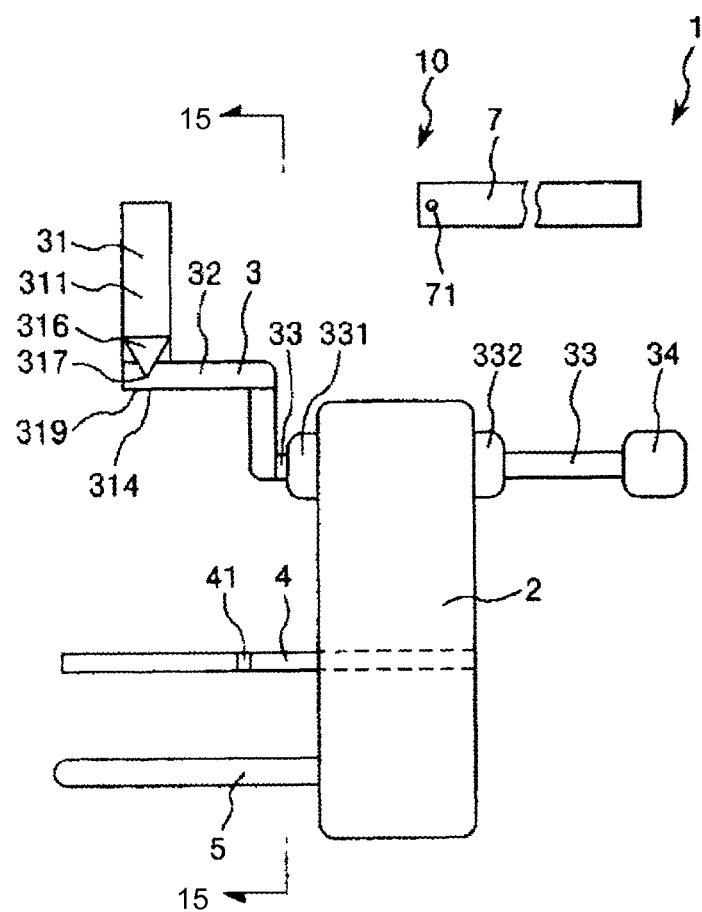
FIG. 14 is a lateral view depicting a second exemplary embodiment of a puncture apparatus of the present disclosure.
Figure 15:
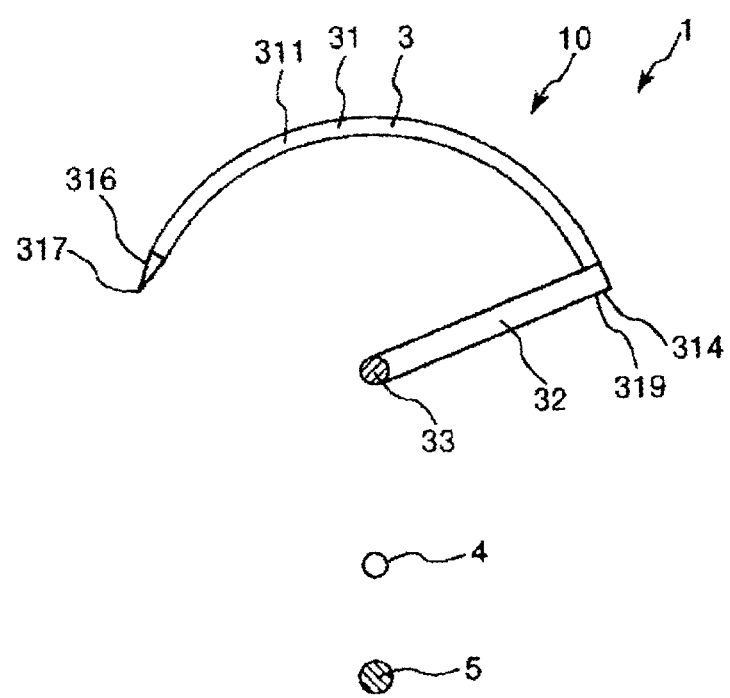
FIG. 15 is a cross sectional view taken along line 15-15 in FIG. 14.

FIG. 14 is a side elevational view depicting a second exemplary embodiment of the puncture apparatus of the present disclosure, and FIG. 15 is a sectional view taken along line 15-15 in FIG. 14.

The following description is given assuming that the left side in FIG. 14 is the "distal end" and the right side is the "proximal end."

In the following, the present exemplary embodiment as shown in FIG. 14 is described principally in regard to differences thereof from the exemplary embodiments described hereinabove while description of similar matters is omitted.

As depicted in FIGS. 14 and 15, in the puncture apparatus 1 of the second embodiment, the puncture needle 31, for example, the needle main body 311 and the extension needle 316, have a flattened shape as viewed in a longitudinal direction of the needle main body 311 and the extension needle 316. In accordance with an exemplary embodiment, transverse sectional shapes of the needle main body 311 and the extension needle 316 correspond to the transverse sectional shape of the main body portion 80 of the biological tissue supporting indwelling article 8.

Consequently, the puncture apparatus 1 can form, in a patient, a through-hole 500 of a shape corresponding to that of the main body portion 80 of the biological tissue supporting indwelling article 8, and the biological tissue supporting indwelling article 8 can be buried more readily and appropriately.

Further, with the puncture apparatus 1, similar effects to those of the first exemplary embodiment described hereinabove can be achieved.

Figure 16:
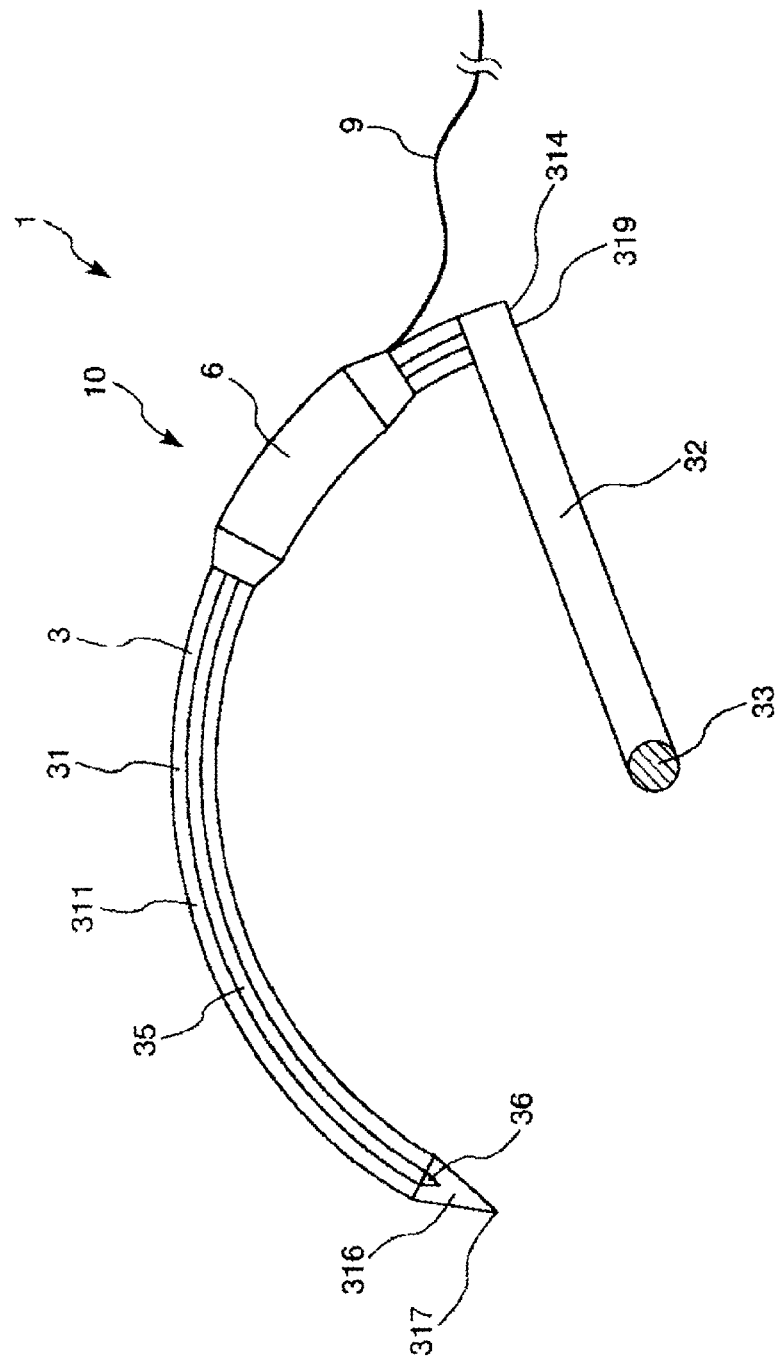
FIG. 16 is a cross sectional view depicting a third exemplary embodiment of a puncture apparatus of the present disclosure.

FIG. 16 is a sectional view depicting a third exemplary embodiment of the puncture apparatus of the present disclosure. FIG. 16 corresponds to FIG. 2 of the first exemplary embodiment disclosed above and depicts a portion of the puncture member.

In the following, the exemplary embodiment as shown in FIG. 16 is described principally in regard to differences thereof from the first exemplary embodiment disclosed hereinabove while description of similar items is omitted.

As depicted in FIG. 16, the puncture apparatus 1 of an exemplary embodiment includes a sheath 6 of a tubular shape provided for movement along a longitudinal direction of the puncture needle 31 of the puncture member 3, and a pusher 9 for pushing the sheath 6 to move in a direction toward the distal end of the puncture needle 31.

The length of the sheath 6 is set shorter than that of the needle main body 311. Further, the sheath 6 has a shape corresponding to a portion of the needle main body 311 and is curved in an arc.

As the pusher 9, a pusher similar to the pusher 7 in the first exemplary embodiment can be used. Further, a distal end as one end portion of the pusher 9 is fixed to a proximal end portion of the sheath 6. Further, graduations not depicted which indicate the position of the sheath 6 with respect to the puncture needle 31 can be provided on the pusher 9.

Further, grooves 35 and 36 are formed on an outer circumferential face of the needle main body 311 and the extension needle 316 along a longitudinal direction of the same. The groove 35 and the groove 36 are formed at positions similar to each other and pass each other when the extension needle 316 is moved in a direction toward the distal end of the needle main body 311 with respect to the needle main body 311. Although the grooves 35 and 36 in the present embodiment individually have a straight shape, the shape of the grooves 35 and 36 is not limited to this, and some other shape such as, for example, a spiral shape may be applied.

In the puncture apparatus 1, for example, if a blood vessel or the like of a patient is punctured by the needle tip 317 of the extension needle of the puncture needle 31 and the patient suffers from bleeding, then the blood flows in a direction toward the proximal end along the grooves 35 and 36. For example, if a back flash of the blood occurs.

Consequently, an operator can grasp or identify that the living body of the patient is bleeding, for example, that a blood vessel or the like of the patient has been punctured by the needle tip 317 of the extension needle.

In this case, the sheath 6 would be pushed in a direction toward the distal end by the pusher 9 so as to move in the direction toward the distal end along the puncture needle 31 until the sheath 6 is arranged at the location at which the patient is bleeding. Consequently, the bleeding can be stopped.

Further, with the puncture apparatus 1, also effects similar to those of the first exemplary embodiment described hereinabove can be achieved.

Note that the sheath 6 may have, for example, a lumen along which liquid such as medical solution is to flow. Further, on a side face of the sheath 6, one or a plurality of side holes communicating with the lumen may be formed.

The means for stopping bleeding is not limited to the sheath 6, and, for example, an expandable and contractible balloon may be provided on the sheath 6.

Although the puncture device and the puncture apparatus of the present disclosure have been described based on the embodiments shown in the drawings, the present disclosure is not limited to them, and the configuration of each unit can be replaced with an arbitrary configuration having a similar function. Further, other arbitrary constructions may be added to the present disclosure.

Further, the present disclosure may be a combination of two or more configurations of the exemplary embodiments disclosed above.

Note that, although the extension needle of the puncture needle in the embodiments disclosed above is inserted in the hollow portion of the needle main body, the puncture needle is not limited to this, and, for example, the needle main body may be inserted in the hollow portion of the extension needle. For example, the outside-inside positional relationship of the needle main body and the extension needle may be reversed to those disclosed in the exemplary embodiments.

Further, in the present disclosure, one of the extension needle and the needle main body may be solid.

Further, in the present disclosure, the extension needle may be inseparable from the needle main body.

Further, in the present disclosure, the puncture needle, for example, the needle main body and the extension needle, may individually have a linear shape.

Further, in the present embodiment, the extension means may be configured such that the extension means pushes the proximal end of the extension needle to move the extension needle.

Further, in the present disclosure, the extension means may be fixedly mounted on or integrated with the extension needle. In this case, the extension means may be fixedly mounted on or integrated with the proximal end side of the extension needle.

Further, in the present disclosure, the biological tissue supporting indwelling article may be accommodated in the hollow portion of the puncture needle.

Further, in the description of the embodiments disclosed above, the puncture device and the puncture apparatus of the present disclosure are applied to an apparatus, which can be used when a biological tissue supporting indwelling article, which can be buried for the treatment of the woman's urinary incontinence, is buried into the living body. However, the application of the puncture device and the puncture apparatus of the present disclosure is not limited to this.

For example, the target of the application of the present disclosure includes an excretory disorder along with the weakening of the pelvic floor muscle group (urinary urgency, frequent urination, urinary incontinence, fecal incontinence, urinary retention, dysuria or the like), and a pelvic floor disorder including pelvic organ prolapse, vesicovaginal fistula, urethrovaginal fistula, pelvic pain or the like. In the pelvic organ prolapse, there are include disorders of cystocele, enterocele, rectocele, hysterocele and the like. Alternatively, there are included disorders of anterior vaginal prolapse, posterior vaginal prolapse, vaginal vault prolapse, vaginal apical prolapse and the like in which the naming method thereof is based on the manipulating vaginal-wall regions.

Also, in the overactive tissues, there are included bladder, vagina, uterus, bowel and the like. In the less active tissues, there are included bones, muscles, fascias, ligaments and the like. In particularly, in the pelvic floor disorders, there are included an obturator fascia, a coccygeus fascia, a cardinal ligament, an uterosacral ligament, a sacrotuberous ligament and the like.

For the procedure for interlocking an overactive tissue in the pelvic floor disorder with the less active tissue, there are included a retropubic sling surgery, a transobturator sling surgery (transobturator sling surgery, transobturator tape: TOT), a tension-free vaginal mesh (Tension-free Vaginal Mesh: TVM) surgery, a uterosacral ligament suspension (Uterosacral Ligament Suspension: USLS) surgery, a sacrospinous ligament fixation (Sacrospinous Ligament Fixation: SSLF) surgery, an iliococcygeus fascia fixation surgery, a coccygeus fascia fixation surgery, and the like.

A puncture device of the present disclosure can include a puncture needle including a needle main body for puncturing a biological tissue, and an extension needle provided for movement relative to the needle main body along a longitudinal direction of the needle main body for puncturing the biological tissue and extension means for moving the extension needle in a direction toward a distal end of the needle main body with respect to the needle main body to extend the puncture needle.

Meanwhile, a puncture apparatus of the present disclosure includes the puncture device of the present embodiment, a urethral-insertion member of a longitudinal shape for being inserted into a urethra and restriction means for restricting a positional relation between the puncture needle and the urethral-insertion member such that, when the puncture needle rotationally moves and punctures the biological tissue, a needle tip of the extension needle passes a farther-position side from a center of the rotational movement of the puncture needle than the urethral-insertion member.

With the present disclosure, a biological tissue supporting indwelling article can be buried into a living body readily, and when the biological tissue supporting indwelling article is buried, the burden on the patient is relatively light and the safety of the patient is relatively high. In addition, the safety of the operator is relatively high. Further, the puncture device and the puncture apparatus can cope also with a patient who has a comparatively thick subcutaneous tissue.

For example, in accordance with an exemplary embodiment, where the puncture apparatus includes the restriction means for restricting the positional relation between the puncture needle and the urethral-insertion member such that, when the shaft portion rotationally moves and the puncture needle punctures the biological tissue, the needle tip of the extension needle passes the farther-position side from the center of a portion, which is curved in an arc, of the extension needle, than the urethral-insertion member, for example, when the puncture apparatus is to be used for the treatment of woman's urinary incontinence, the urethral-insertion member of the puncture apparatus is inserted into a urethra, and the puncture needle is rotationally moved so that the living body is punctured by the puncture needle. Thereupon, since the needle tip of the extension needle passes the farther-position side from the center of the extension needle than the urethral-insertion member, the puncture needle can puncture the living body avoiding the urethra. Consequently, the puncture needle can be prevented from puncturing the urethra. In addition, it can help prevent a fingertip of the operator from being punctured by the puncture needle.

Further, since the puncture needle can be extended, the puncture device and the puncture apparatus can cope with a patient who has a comparatively thick subcutaneous tissue.

Further, when the biological tissue supporting indwelling article for the treatment of urinary incontinence is to be buried, no incision of the vaginal wall is required, and the biological tissue supporting indwelling article can be buried by a low invasive manual procedure. Further, such a situation that, as in a case in which the vagina is incised, the biological tissue supporting indwelling article is exposed to the inside of the vagina through a wound caused by the incision or that such complications as an infection from the wound occur can be prevented. Therefore, the biological tissue supporting indwelling article can be buried in very high safety and with certainty.

The detailed description above describes a puncture instrument and puncture device. The disclosure is not limited, however, to the precise embodiments and variations described. Various changes, modifications and equivalents can effected by one skilled in the art without departing from the spirit and scope of the disclosure as defined in the accompanying claims. It is expressly intended that all such changes, modifications and equivalents which fall within the scope of the claims are embraced by the claims.

What is claimed is:

1. A puncture device comprising:
   a puncture needle for puncturing a biological tissue, the puncture needle including a needle main body and an extension needle having a needle tip, wherein the extension needle moves relative to the needle main body along a longitudinal direction of the needle main body for puncturing the biological tissue, and wherein the extension needle has a hollow portion extending to a proximal end of the needle tip of the extension needle, and the needle tip has an attachment portion formed over a circumference on an outer periphery of the proximal end of the needle tip such that the extension needle is configured to move integrally with the needle main body during an initial state and relative to the needle body in an extension state, and wherein the needle main body and the extension needle each have a portion, which is curved in an arc along a longitudinal direction of the needle main body and the extension needle; and
   extension means for moving the extension needle in a direction toward a distal end of the needle main body with respect to the needle main body to extend the puncture needle, and wherein the extension means is inserted into the hollow portion of the extension needle to push a distal end portion of the extension needle to move the extension needle.

2. The puncture device according to claim 1, wherein the needle main body has a hollow portion; and the extension needle is inserted in the hollow portion of the needle main body for movement along the longitudinal direction of the needle main body.

3. The puncture device according to claim 2, wherein
the needle main body has, at the distal end of the needle main body, an opening which communicates with the hollow portion; and
the extension needle has, at a distal end of the extension needle, the needle tip capable of puncturing the biological tissue, the needle tip protruding from the opening of the needle main body when the extension needle is positioned on a most proximal end side with respect to the needle main body.

4. The puncture device according to claim 2, wherein the extension means has an elongated form.

5. The puncture device according to claim 1, comprising:
an elongated biological tissue supporting indwelling article for being buried into a living body and supporting a biological tissue.

6. The puncture device according to claim 5, wherein the extension means has, at a distal end portion of the extension means, an engaging portion for engaging with the biological tissue supporting indwelling article.

7. The puncture device according to claim 1, wherein the extension needle is separable from the needle main body.

8. The puncture device according to claim 1, wherein the needle main body and the extension needle each have a flattened shape as viewed in a longitudinal direction of needle main body and the extension needle.

9. The puncture device according to claim 1, wherein the needle main body and the extension needle are individually provided for rotational movement.

10. The puncture device according to claim 1, wherein the proximal end of the needle tip is at the distal end portion of the extension needle.

11. The puncture device according to claim 1, wherein an angle of the arc of the needle main body is 95 degrees to 180 degrees, and an angle of an arc of the puncture needle in a state in which the puncture needle is extended is 190 degrees to 270 degrees.

12. A puncture apparatus comprising:
a puncture needle including a needle main body for puncturing a biological tissue, and an extension needle provided for movement relative to the needle main body along a longitudinal direction of the needle main body for puncturing the biological tissue, and extension means for moving the extension needle in a direction toward a distal end of the needle main body with respect to the needle main body to extend the puncture needle, wherein the needle main body and the extension needle each have a curved portion along a longitudinal direction of the needle main body and the extension needle, and the needle main body and the extension needle are individually provided for rotational movement;
a urethral-insertion member of a longitudinal shape for being inserted into a urethra; and
restriction means for restricting a positional relation between the puncture needle and the urethral-insertion member such that, when the puncture needle rotationally moves and punctures the biological tissue, a needle tip of the extension needle passes from a center of the rotational movement of the puncture needle beyond the urethral-insertion member.

13. The puncture apparatus according to claim 12, further comprising:

a vaginal insertion member of a longitudinal shape for being inserted into a vagina, wherein the restriction means restricts the positional relation between the puncture needle and the vaginal insertion member such that, when the puncture needle rotationally moves and punctures the biological tissue, the needle tip of the extension needle does not collide with the vaginal insertion member.

14. The puncture device according to claim 13, wherein
the puncture device has a shaft portion serving as a rotational shaft for the rotational movement; and
the restriction means includes supporting members which support the shaft portion for rotational movement and respectively support the urethral-insertion member and the vaginal insertion member.

15. A puncture device comprising:
a puncture needle for puncturing a biological tissue, the puncture needle including a needle main body, and an extension needle having a needle tip, wherein the extension needle moves relative to the needle main body along a longitudinal direction of the needle main body for puncturing the biological tissue, and wherein the extension needle has a hollow portion extending to a proximal end of the needle tip of the extension needle, and wherein the needle tip has an attachment portion formed over a circumference on an outer periphery of the proximal end of the needle tip such that the extension needle is configured to move integrally with the needle main body during an initial state and relative to the needle body in an extension state, and wherein the needle main body and the extension needle each have a portion, which is curved in an arc along a longitudinal direction of the needle main body and the extension needle; and
a pusher for moving the extension needle in a direction toward a distal end of the needle main body with respect to the needle main body to extend the puncture needle, and wherein the pusher is inserted into the hollow portion of the extension needle and configured to push a distal end portion of the extension needle.

16. The puncture device according to claim 15, wherein
the needle main body has a hollow portion;
the extension needle is inserted in the hollow portion of the needle main body for movement along the longitudinal direction of the needle main body;
the needle main body has, at the distal end of the needle main body, an opening which communicates with the hollow portion; and
the extension needle has, at a distal end of the extension needle, the needle tip capable of puncturing the biological tissue, the needle tip protruding from the opening of the needle main body when the extension needle is positioned on a most proximal end side with respect to the needle main body.

17. The puncture device according to claim 15, wherein the proximal end of the needle tip is at the distal end portion of the extension needle.

18. The puncture device according to claim 15, wherein an angle of the arc of the needle main body is 95 degrees to 180 degrees, and an angle of an arc of the puncture needle in a state in which the puncture needle is extended is 190 degrees to 270 degrees.

19. A method of forming a path in living body tissue comprising:
inserting a urethral-insertion member of a longitudinal shape inserted into a urethra;

placing a puncture needle of a puncture device into a portion of a living body, the puncture needle including a needle main body for puncturing a biological tissue, and an extension needle having a needle tip, wherein the extension needle moves relative to the needle main body along a longitudinal direction of the needle main body for puncturing the biological tissue, and wherein the extension needle has a hollow portion extending to a proximal end of the needle tip of the extension needle, and the needle tip has an attachment portion formed over a circumference on an outer periphery of the proximal end of the needle tip such that the extension needle is configured to move integrally with the needle main body during an initial state and relative to the needle main body in an extension state, and wherein the needle main body and the extension needle each have a portion, which is curved in an arc along a longitudinal direction of the needle main body and the extension needle;

restricting a positional relation between the puncture needle and the urethral-insertion member such that, when the puncture needle rotationally moves and punctures the biological tissue, the needle tip of the extension needle passes from a center of the rotational movement of the puncture needle beyond the urethral-insertion member; and pushing a distal end portion of the extension needle in a direction toward a distal end of the needle main body with respect to the needle main body to extend the extension needle into the living body, and wherein the extension needle moves integrally with the needle main body during the initial state and relative to the needle main body in the extension state.

20. The method according to claim 19, wherein the needle main body has, at the distal end of the needle main body, an opening which communicates with the hollow portion; and the extension needle has, at a distal end of the extension needle, the needle tip capable of puncturing the biological tissue, the needle tip protruding from the opening of the needle main body when the extension needle is positioned on a most proximal end side with respect to the needle main body.

* * * * *